United States Patent [19]

Jolly

[11] Patent Number: 5,559,035
[45] Date of Patent: Sep. 24, 1996

[54] SOLID PHASE CALIBRATION STANDARDS

[75] Inventor: Clifford D. Jolly, Lakewood, Colo.

[73] Assignee: Umpqua Research Company, Myrtle Creek, Oreg.

[21] Appl. No.: 351,544

[22] Filed: Dec. 7, 1994

Related U.S. Application Data

[63] Continuation of Ser. No. 181,354, Jan. 12, 1994, abandoned, which is a continuation of Ser. No. 934,420, Aug. 24, 1992, abandoned.

[51] Int. Cl.$^6$ ................................................ G01N 31/00
[52] U.S. Cl. ................................................ 436/19; 436/8
[58] Field of Search ................................. 436/8, 18, 19, 436/73, 127, 163, 174

[56] References Cited

U.S. PATENT DOCUMENTS

| | | | |
|---|---|---|---|
| 3,608,836 | 9/1971 | Bryant et al. | 241/16 |
| 3,706,634 | 12/1972 | Kowalski | 204/46 |
| 3,951,797 | 4/1976 | Seely | 210/63 |
| 3,954,510 | 5/1976 | Gunn et al. | 148/6.2 |
| 4,008,144 | 2/1977 | Torikai et al. | 204/290 R |
| 4,110,400 | 8/1978 | Jha et al. | 423/141 |
| 4,123,290 | 10/1978 | Kennedy | 148/6.2 |
| 4,152,252 | 5/1979 | Tolley et al. | 209/10 |
| 4,247,465 | 1/1981 | Kao et al. | 260/340.2 |
| 4,289,648 | 9/1981 | Hoskins et al. | 422/61 |
| 4,601,805 | 7/1986 | Palvadeau et al. | 204/255 |
| 4,793,929 | 12/1988 | Kickuth et al. | 210/602 |
| 4,935,373 | 6/1990 | Christiansen | 436/18 |
| 4,971,635 | 11/1990 | Guhde et al. | 148/267 |
| 5,039,492 | 8/1991 | Saaski et al. | 422/55 |
| 5,080,805 | 1/1992 | Houser | 210/722 |

OTHER PUBLICATIONS

Fisher Catalog 1988, Fisher Scientific "Fisher Biotech Organic and Inorganic Buffers", pp. 1325–1327.
The Merck Index, 10th Edition, Merck & Co. Inc. 1983. p. 811.
Aldrich Catalog of Fine Chemicals. pp. 135, 292, 401 and 914. 1988–89.
Baxter Scientific Products General Catalog 1991–1992 pp. 2204, 2218, 2231, 2277, 2280, 2294, 2366.
"An Internal Standard Solution . . . " Nuyama, Yasushi et al. Jpn. Kokai Tokkyo Koho 1987.
"Determination of Cyanide in water" Yui, Hai Yiu, Fen Hsi Hua Hsueh 8(1)73–6 1980.
"Ionization Constants of benzoic acid . . . " Schwitzgebel, G., Z. Phys. Chem (Wqesbaden), 125(1), 1–5 1981.
CRC Handbook of Chemistry and Physics. 63rd edition, 1982–1983 selected pages of Table B.

*Primary Examiner*—James C. Housel
*Assistant Examiner*—Rachel Heather Freed
*Attorney, Agent, or Firm*—Chernoff, Vilhauer, McClung & Stenzel

[57] ABSTRACT

Solid phase ionic calibration standards are disclosed that comprise sparingly and selectively soluble solids. The calibration standards are especially useful in calibration pH electrodes used to monitor weak ionic strength solutions, and permit rapid pH electrode recovery times.

1 Claim, 2 Drawing Sheets

ON
SOLID PHASE CALIBRATION STANDARDS

This is a continuation of application Ser. No. 08/181,354 filed on Jan. 12, 1994, now abandoned, which is a continuation of Ser. No. 07/934,420 filed on Aug. 24, 1992, now abandoned.

BACKGROUND OF THE INVENTION

On-line sensors to assess the chemical characteristics of fluid streams are in common use. Calibration and recalibration of such chemical sensors has typically been accomplished off-line, for example, by placing a pH electrode in separate buffer solutions of known pH. Such off-line calibration suffers from a number of drawbacks, including lack of automation and, in some cases, accuracy due to electrode hysteresis. Current methods of on-line pH calibration typically utilize buffered solutions of known pH and generally high ionic strength. Low ionic strength buffers are not used because they are not stable. The problem with the use of such high ionic strength solutions for on-line calibration is that due to their high concentration of ions, an unacceptably long period of time is required for the pH electrode to regain its sensitivity and thus its measuring or sensing capacity, often referred to as "recovery time". In the case of measurement of low ionic strength sample solutions, this recovery time problem is especially egregious as the recovery time is especially long (often a matter of hours) due to the very large ionic strength differential between the calibrating buffered solution and the solution whose ionic strength is to be determined. U.S. Pat. No. 4,713,618 discloses an on-line system for calibrating pH sensors comprising the use of a solution of concentrated acid or base to condition the fluid to a predetermined pH level. Shortcomings of such a conditioning solution include the same recovery time problem mentioned above, the relatively large volume of solution needed and the need for a diffusion chamber.

There is therefore a need in the chemical sensor calibration art for a simple, reliable, space-saving calibration standard that may be used both on-line and off-line and that permits quick recovery of a chemical sensor's capacity to measure. These needs and others, which will be apparent to those skilled in the art, are met by the present invention, which is summarized and described in detail below.

SUMMARY OF THE INVENTION

There are essentially three aspects to the present invention. In a first aspect, there is provided a solid phase calibration standard (SPCS) for selectively imparting a predetermined chemical characteristic to a fluid stream by dissolution, comprising a solid that is sparingly and selectively soluble in the fluid stream. In a second aspect, the same SPCS may be used as a standard for calibrating an on-line or off-line sensor of a predetermined chemical characteristic of a fluid stream. In a third aspect, there is provided a calibration system that utilizes the SPCS to impart a predetermined level of a selected chemical characteristic to a fluid sample stream.

DETAILED DESCRIPTION OF THE INVENTION

Figure 1:
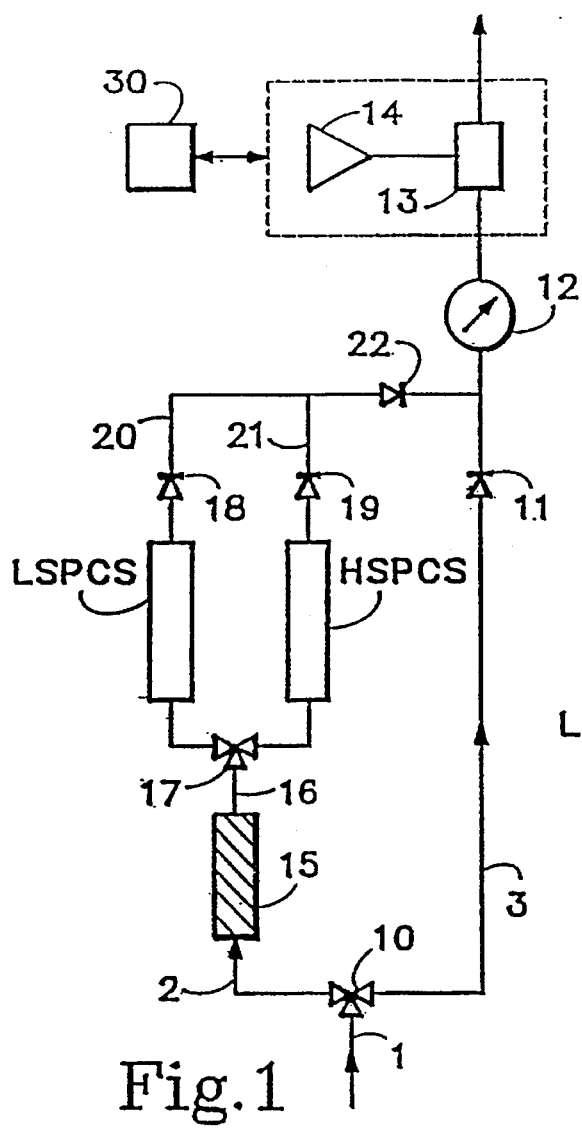
FIG. 1 is a flow schematic showing an exemplary use of the SPCS of the present invention in a system for on-line calibration of a chemical sensor.

According to the present invention, there is provided a SPCS both for imparting a predetermined chemical characteristic to a fluid stream and for calibrating both on-line and off-line sensors of a given chemical characteristic of a fluid stream. The SPCS is useful in both an on-line and an off-line calibration system for a wide variety of chemical sensors. As mentioned in the Summary above, the SPCS broadly comprises a sparingly and selectively soluble solid.

In a preferred application, the chemical characteristic of concern is pH, the fluid stream is water, and the solid is selected from basic metal oxides, acidic metal oxides, amphoteric metal oxides, isopoly-acids of metals, heteropolyacids of metals, metal carbonates, benzoic acid, and halogen-substituted benzoic acids. Especially preferred SPCS in such pH sensor applications are $BaCo_3$, $CaCO_3$, $CuCO_3$, $MgO$, $MoO_3$, $H_2MoO_4$, $H_2Mo_4O_{13}$, $PbCO_3$, $SnO_2$, $H_2WO_4$, $ZnO$, and 4-iodobenzoic acid.

The SPCS of the present invention is also capable of calibrating sensors that measure total organic carbon (TOC) and total inorganic carbon (TIC) content. In the case of TOC, the SPCS is preferably selected from benzoic acid and 4-iodobenzoic acid. In the case of TIC, the SPCS may comprise any of the semi-soluble or even relatively insoluble metal carbonates of Ba, Ca, Cu, Mg, Pb, Sr, Zn, and Zr. Especially preferred carbonates for TIC measurement are $BaCO_3$, $CaCO_3$, $CuCO_3$, and $PbCO_3$. The solubility of such carbonates may be adjusted by pH adjustment upstream of the standard. This may be accomplished by installing a SPCS bed that produces the desired pH in front of the carbonate TIC calibration SPCS. Low pH causes carbonate concentration and thus TIC to increase.

In a closely related aspect of the present invention, there is provided a system for on-line calibration of a chemical sensor, comprising: a sensor for sensing the level of a selected chemical characteristic of a fluid stream and producing an output representative of the sensed level of the selected chemical characteristic; means for supplying an influent fluid sample stream at a predetermined volumetric rate; at least one solid phase standard means for imparting to the influent fluid sample stream a predetermined level of the selected chemical characteristic; means selectively operable to establish first and second fluid sample stream flow paths, the first flow path providing the influent fluid sample stream to the sensor, and the second flow path directing the influent fluid sample stream to and through the solid phase standard means to said sensor; and means for calibrating the output representative of the sensed level of the selected chemical characteristic with respect to the predetermined level of the selected chemical characteristic in the influent fluid sample stream after the same has been directed through the solid phase standard means. In a preferred embodiment of such a system, there is included means for preconditioning the influent fluid stream to adjust the pH to a desired value, or to remove impurities from the stream. The removal of impurities is important so as to allow the SPCS to dictate the ionic strength of the feed solution. In an especially preferred embodiment, the preconditioning means comprises a bed or column of ion-exchange resin.

Such a system is exemplified in FIG. 1, where there is shown a schematic of an influent sample or process fluid stream 1 that may flow either through calibration line 2 or sample line 3, normally the latter. When fluid stream 1 flows in sample line 3, it is in fluid communication through diverter valve 10 and check valve 11 with a flow meter 12 (optional) and a chemical sensor 13. Sensor 13 generates an output representative of the sensed chemical characteristic, and the output is displayed and/or stored on or in a meter 14, the output in turn being monitored either visually or by a microcomputer (not shown). A calibration adjustment system 30 is in feedback and input communication with the sensor 13 and meter 14, indicated by the double-headed arrow and dashed lines. Adjustment of the calibration set point(s) may be by manual adjustment of the meter 14 or by microcomputer for remote calibration. The fluid stream 1 may be diverted, by diverter valve 10, to be in fluid communication with a preconditioning bed 15, such as an ion exchange bed, and then by diverter valve 17, to be in fluid communication with either of two solid phase calibration standards, designated "LSPCS" (for low levels of sensed chemical characteristic, such as for low pH) and "HSPCS" (for high levels of sensed chemical characteristic, such as for high pH). A preferred design of the SPCS is a flow-through cartridge containing the solid material of the standard. Fluid flowing through either the LSPCS or the HSPCS dissolves the solid phase standard to a limited extent, imparting a known and precise ion concentration to the effluent 20 or 21, which can be placed in fluid communication with the flowmeter 12 and/or the sensor 13 via check valves 18, 19 and 22. It is to be understood that only one, two or more SPCS's may be used if desired, to provide any number of calibration points.

Figure 2:
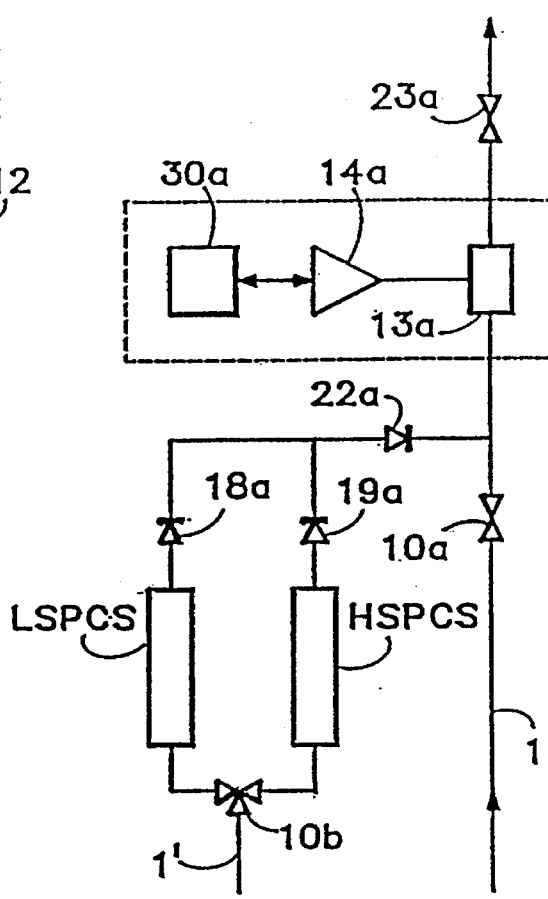
FIG. 2 is another flow schematic of an alternative embodiment of the present invention.

An alternative embodiment of a system incorporating two SPCS's of the present invention is illustrated in FIG. 2, wherein like numerals generally designate the same elements as in FIG. 1. An influent sample or process stream 1 flows through valve 10a that is normally open, thence through pH sensor 13a. Sensor 13a generates representative output, which is displayed and/or stored on or in meter 14a, the output being monitored as explained in connection with FIG. 1. Part of the system is a calibration adjustment system 30a, which functions in substantially the same manner shown and described in connection with FIG. 1. When calibration is desired, valves 10a and 23a are closed, valves 10b (normally closed) is opened, and fluid. 1' of a known and preferably low ionic strength is permitted to flow through either the LSPCS or the HSPCS, its flow to sensor 13a being controlled by check valves 18a, 19a and 22a.

Figure 3:
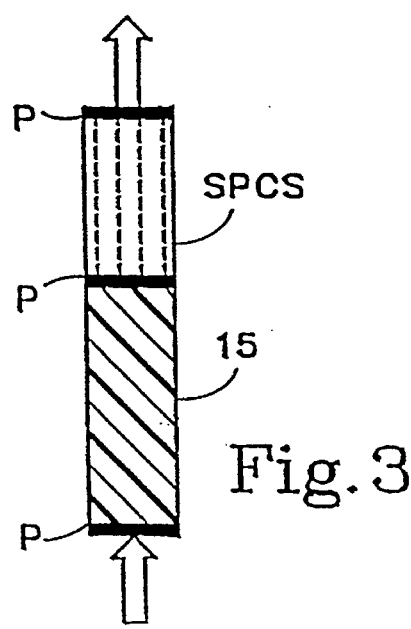
FIG. 3 is a cross-sectional schematic of an exemplary embodiment of the SPCS of the present invention.

FIG. 3 represents an alternative embodiment of the SPCS of the invention, which incorporates a solid preconditioner 15, such as an ion exchange resin, into a cartridge, upstream of SPCS.

In its simplest form, the SPCS of the invention may be prepared by simply packing into a column or cartridge housing 20–100 mesh granules of the solid by itself or with any inert material that is compatible with the intended application, such as porous frits or screens ("p" in FIG. 3) or glass wool.

EXAMPLE 1

Two solid phase calibration standards for calibration of an on-line pH sensor were fabricated and incorporated into an on-line system of substantially the same arrangement shown in FIG. 2. One solid phase calibration standard, for high pH (10.35) (designated "HSPCS"), comprised granules of MgO 20–100 mesh in a 6 cc cylindrical stainless steel flow-through module. The other for low pH (3.40) (designated "LSPCS"), comprised granules of $MoO_3$, 100–200 mesh. Process fluid stream 1 comprised either tap water or deionized water. Calibration fluid stream 1' comprised either deionized water or commercially available distilled water having a specific conductance of $\leq 5$ micromho/cm. The system was run continuously with calibration being conducted manually every few days for a little over 5 weeks. Flow rates varied from 1 to 10 ml/min and calibration was checked against fresh buffer solutions using the following protocol.

Referring to FIG. 2, diverter valve 10b was opened to place the calibration fluid stream 1' in fluid communication with the HSPCS module and the stream was allowed to flow therethrough and through pH sensor 13a for approximately 6 to 8 minutes to allow the pH meter to stabilize. The pH meter 14a was then calibrated to read pH 10.35. Diverter valve 10b was then closed relative to the HSPCS module and opened relative to the LSPCS module for the same approximate time and the pH meter was calibrated to read pH 3.40. Valve 10b was then closed and valve 10a was opened to permit process fluid stream 1 to flow. Fresh pH 10.00, 7.00, and 4.00 buffer solutions were then successively fed through the process fluid stream 1 to check the pH sensor calibration and the measured values were recorded. (The order of the pH check feeds may be varied as desired.) Process fluid stream 1 is then again allowed to flow through valve 10a until the next calibration cycle.

The results, showing excellent agreement with the commercial buffer standards ($\pm 0.1$ pH unit), are shown in Table 1.

TABLE 1

| Test Day | Flow Rate (ml/min) | Measured Value Before Recalibration | | Calibration Check | | |
|---|---|---|---|---|---|---|
| | | HPSCS (pH 10.35) | LSPCS (pH 3.40) | Commercial pH 4 Buffer | Commercial pH 7 Buffer | Commercial pH 10 Buffer |
| 1 | 2.0 | 10.37 | 3.36 | 3.94 | 6.98 | — |
| 2 | 2.0 | — | — | 3.90 | 7.01 | 10.05 |
| 5 | 1.1 | 10.33 | 3.32 | 3.92 | 7.01 | 10.08 |
| 6 | 1.5 | — | — | 3.96 | 6.96 | — |
| 7 | 10.0 | — | — | 3.85 | 7.05 | — |
| 7 | 1.5 | 10.42 | 3.38 | 3.97 | 7.05 | — |
| 8 | 1.5 | 10.42 | 3.23 | 4.09 | 7.05 | — |

TABLE 1-continued

| | | Measured Value | | Calibration Check | | |
| | | Before Recalibration | | Commercial | Commercial | Commercial |
| Test Day | Flow Rate (ml/min) | HPSCS (pH 10.35) | LSPCS (pH 3.40) | pH 4 Buffer | pH 7 Buffer | pH 10 Buffer |
| --- | --- | --- | --- | --- | --- | --- |
| 9  | 1.0 | 10.38 | 3.26 | —    | 7.08 | —     |
| 13 | 1.5 | 10.48 | 3.52 | 3.97 | 7.01 | —     |
| 14 | 1.1 | 10.33 | 3.50 | 4.00 | 7.00 | —     |
| 15 | 1.1 | —     | —    | 4.02 | 7.04 | —     |
| 18 | 1.1 | 10.55 | 3.55 | —    | 7.09 | —     |
| 19 | 1.5 | 10.38 | 3.50 | 4.08 | 7.08 | —     |
| 22 | 1.5 | 10.37 | 3.55 | 3.97 | 7.01 | —     |
| 23 | 1.0 | 10.52 | 3.64 | 3.90 | 6.94 | 9.99  |
| 26 | 2.3 | 10.05 | 3.99 | 3.91 | 7.08 | 10.28 |
| 27 | 1.0 | —     | —    | 3.98 | 7.03 | 10.04 |
| 29 | 1.9 | 10.27 | 3.57 | 3.90 | 7.00 | —     |
| 33 | 1.1 | 10.30 | 3.61 | 4.02 | 7.06 | —     |
| 34 | 1.1 | 10.40 | 3.53 | 3.86 | 6.95 | 10.04 |
| 35 | 1.1 | 10.01 | 3.30 | 3.98 | 7.07 | —     |
| 36 | 1.1 | 10.44 | 3.34 | 3.95 | 7.00 | 10.02 |

EXAMPLE 2

Figure 4:
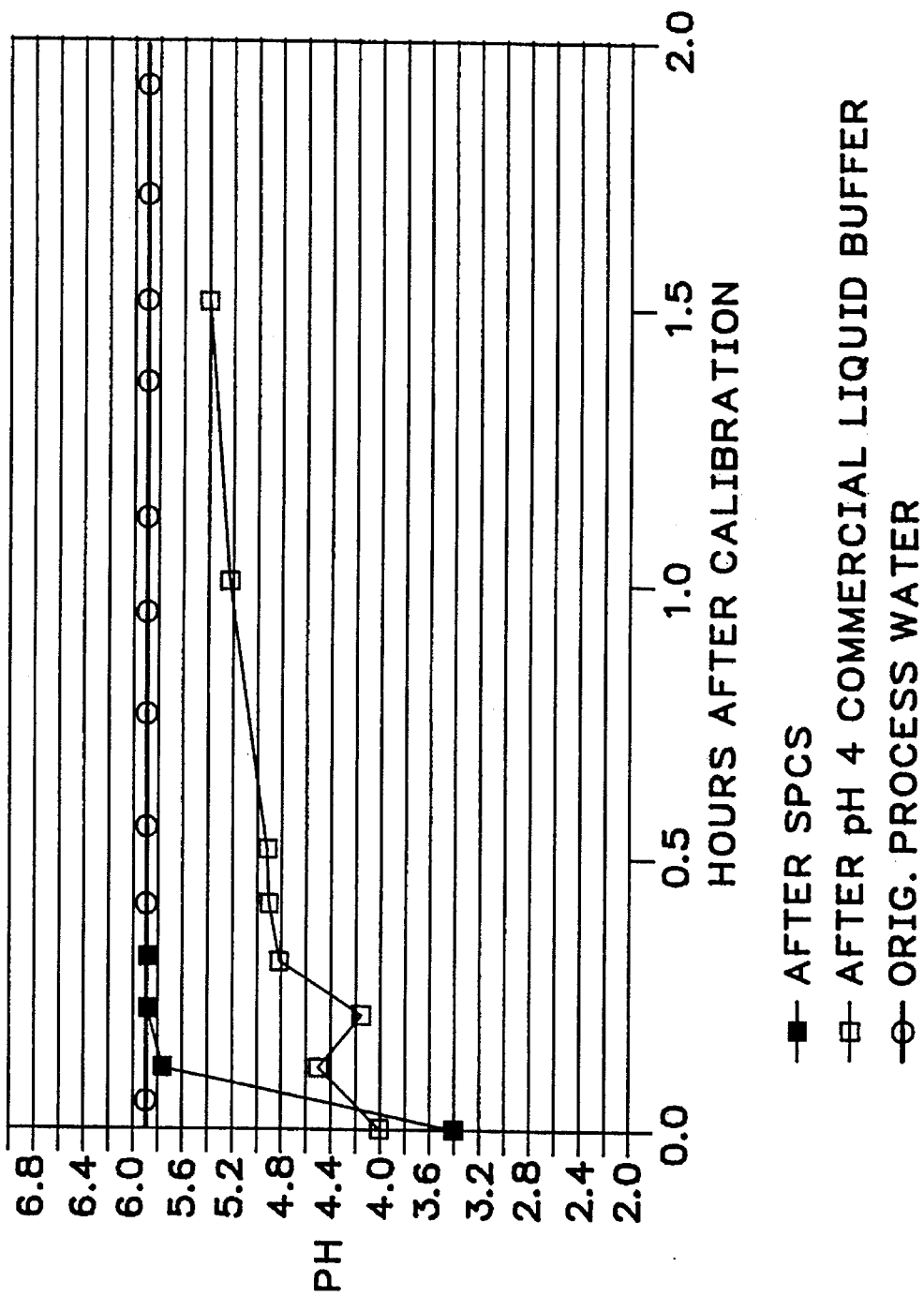
FIG. 4 is a graph showing sensor recovery times after calibration by the SPCS of the present invention as compared with calibration by a conventional liquid phase standard.

The effect of the ionic strength of the calibration solution on electrode response was demonstrated, by calibrating a 50 ml volume pH electrode with an LSPCS of the present invention of substantially the same make-up as in Example 1 on the one hand, and a commercial buffered solution of pH 4.0 on the other. The process fluid feed stream was deionized tap water having a pH of 5.7, and the flow rate was 1 ml/min in a system of substantially the same configuration as shown in FIG. 2. The graph comprising FIG. 4 shows the difference in recovery time of the same pH electrode after being subjected to the commercial buffered solution and to the LSPCS of the present invention. The data show that after calibration with the low ionic strength solution resulting from the LSPCS of the present invention, the electrode takes only 12–15 minutes' recovery time to give an accurate reading of the feed stream pH, whereas the same electrode takes at least 1.5 to 2 hours to return to within 0.5 pH unit of the feed stream pH.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A method of preparing a non-buffered, low ionic strength aqueous calibration fluid, comprising contacting an aqueous fluid stream having a specific conductance of $\leq 5$ micromho/cm with at least one compound selected from the group consisting of basic metal oxides, acidic metal oxides, amphoteric metal oxides, isopolyacids of metals, heteropolyacids of metals and carbonates of metals selected from the group consisting of barium, calcium, copper, molybdenum and lead.

* * * * *

UNITED STATES PATENT AND TRADEMARK OFFICE
CERTIFICATE OF CORRECTION

PATENT NO. : 5,559,035

DATED : September 24, 1996

INVENTOR(S) : Clifford D. Jolly

It is certified that error appears in the above-indentified patent and that said Letters Patent is hereby corrected as shown below:

Col. 3, line 48: delete "fluid. 1' " insert -- fluid --.

Col. 4, line at 60:

Col. 3 of Table:
delete "HPSCS" insert -- HSPCS --.

Col. 5, line at 7: delete "HPSCS" insert -- HSPCS --.

Col. 5, line 39: delete "minutes'" insert -- minutes --.

UNITED STATES PATENT AND TRADEMARK OFFICE
CERTIFICATE OF CORRECTION

PATENT NO. : 5,559,035
DATED : September 24, 1996
INVENTOR(S) : Clifford D. Jolly It is certified that error appears in the above-indentified patent and that said Letters Patent is hereby corrected as shown below:

Col. 5, line 42: after "pH" insert -- (measured in parallel on previously calibrated and recovered electrode) --.

Signed and Sealed this

Fourth Day of February, 1997

Attest:

BRUCE LEHMAN

Attesting Officer

Commissioner of Patents and Trademarks